United States Patent [19]

Williams et al.

[11] Patent Number: 5,756,526
[45] Date of Patent: May 26, 1998

[54] TREATMENT AND PROTECTION OF MINERAL SLURRIES

[75] Inventors: Terry Michael Williams, Ambler; Dolores Ann Shaw, Collegeville; Beverly Jean El'Amma, Perkiomenville, all of Pa.; Dennis Allen Poole, Pemberton, N.J.

[73] Assignee: Rohm and Haas Company, Philadelphia, Pa.

[21] Appl. No.: 655,508

[22] Filed: May 30, 1996

Related U.S. Application Data

[62] Division of Ser. No. 470,195, Jun. 6, 1995, abandoned, which is a division of Ser. No. 166,411, Dec. 10, 1993, abandoned.

[51] Int. Cl.[6] .................. A01N 43/80; A01N 59/00; A01N 59/06; A01N 31/02

[52] U.S. Cl. .................. 514/373; 514/372; 514/714; 514/970; 424/613; 424/682; 424/718; 210/755; 210/764; 422/32; 422/37

[58] Field of Search .................. 514/372, 373, 514/714, 970; 424/718, 613, 682; 210/753, 754, 755, 759, 764; 106/18.33; 422/32, 37; 501/148

[56] References Cited

U.S. PATENT DOCUMENTS

| | | | |
|---|---|---|---|
| 3,870,795 | 3/1975 | Miller et al. | 424/270 |
| 4,067,878 | 1/1978 | Miller et al | 260/302 |
| 5,496,398 | 3/1996 | Drew et al. | 106/15.05 |
| 5,512,213 | 4/1996 | Paterson | 252/400.62 |
| 5,599,827 | 2/1997 | Gironda | 514/372 |

*Primary Examiner*—John Pak
*Attorney, Agent, or Firm*—Julie J.L. Cheng

[57] ABSTRACT

Method of preserving mineral slurries from microbiological attack comprising introducing a nitrite or TBIP followed by sufficient 3-isothiazolone biocide to protect the slurry from attack. Mineral slurries which are so protected are also disclosed.

9 Claims, No Drawings

TREATMENT AND PROTECTION OF MINERAL SLURRIES

This is a divisional of application Ser. No. 08/470,195, filed Jun. 6, 1995, now abandoned, which in turn is a divisional of application Ser. No. 08/166,411 filed on Dec. 10, 1993, now abandoned.

BACKGROUND OF THE INVENTION

1. Field of the Invention

This invention relates to the field of preservation of mineral slurries from microbial attack.

2. Description of the Prior Art

Mineral slurries are used widely as coatings and fillers in the paper industry, and are typically supplied as slurries, i.e., aqueous suspensions, to paper mills. They are also used in the pottery industry.

Mineral slurries are subject to microbial attack and, therefore, are usually protected with a biocide. One of the best class of biocides for protecting mineral slurries is 3-isothiazolone compounds. However, 3-isothiazolone biocide compounds are degraded by sulfites or bisulfites which are typically present in such mineral slurries unless the slurry is pretreated. The state of the art pretreatment is to introduce hydrogen peroxide. However, if excess hydrogen peroxide is used, the 3-isothiazolone biocide which is subsequently introduced can be inactivated.

SUMMARY OF THE INVENTION

It is an object of the present invention to provide an improved method of protecting mineral slurries from microbial attack.

It is another object of the invention to provide mineral slurries which are effectively and efficiently protected from microbial attack.

These objects, and others which will become apparent from the following disclosure, are achieved by the present invention which comprises in one aspect a method of treating and preserving mineral slurries containing nucleophiles comprising introducing nitrite ion or tert-butyl hydroperoxide ("TBHP") and thereafter introducing a microbicidally-effective amount of 3-isothiazolone biocide.

In another aspect the invention comprises mineral slurry, a microbicidally effective amount of 3-isothiazolone biocide, and essentially no nucleophile.

DETAILED DESCRIPTION AND THE PREFERRED EMBODIMENTS

The term "mineral slurries" as used herein is intended to encompass, but not be restricted to, clay slurries such as kaolin, bentonite and attapulgite clays; pigment slurries, such as titanium dioxide slurries; and carbonate slurries.

The term "biocide effectiveness" as used herein is intended to indicate a measure of how long sufficient 3-isothiazolone biocide remains in the slurry to protect the slurry from microbial attack.

Mineral slurries typically contain nucleophiles which are known to attack biocides. Examples of such nucleophiles are sulfite or bisulfite ions, and are most typically bisulfites.

According to the present invention, we introduce nitrite ion or TBHP in order to quench the nucleophiles, and thereafter we introduce a microbicidally-effective amount of 3-isothiazolone biocide.

The nitrite ion is preferably introduced in the form of a nitrite compound selected from the group consisting of sodium nitrite, calcium nitrite, and potassium nitrite. Sodium nitrite is most preferred because it has FDA approval for clay slurries.

The nitrite compound is preferably introduced in an amount of about 10 to 2000 ppm by weight based on slurry, most preferably in an amount of about 100 to 200 ppm. The TBHP is preferably introduced in an amount of about 10 to 2000 ppm by weight based on slurry, most preferably in an amount of about 25 to 750 ppm, and even more preferably in an amount of about 50 to 500 ppm.

Sufficient time is preferably allowed for the quench step, and generally the biocide is introduced at least 10 minutes, preferably about 15 to 40 minutes, after the nitrite ion or TBHP is introduced.

Preferably the temperature of the mineral slurry during the quench step is at least 30° C. and most preferably 40° C.

Preferred 3-isothiazolone biocides are 3-isothiazolone compounds, especially 5-chloro-2-methyl-3-isothiazolone ("CMI"); 2-methyl-3-isothiazolone ("MI"); 2-n-octyl-3-isothiazolone; 4,5-dichloro-2-n-octyl-3-isothiazolone; benzisothiazolone; and 2-methyl-4,5-trimethylene-3-isothiazolone.

The biocide is preferably introduced in an amount of about 1 to 150 ppm, more preferably about 3 to 35 ppm, by weight based on slurry.

The resultant mineral slurry comprises a microbicidally effective amount of 3-isothiazolone biocide, and essentially no nucleophile. The nitrite or TBHP is generally used in excess versus the amount needed to quench the nucleophiles, but is no longer needed in the mineral composition, so if no excess is used, the mineral slurry does not suffer in properties. The mineral slurry composition and process of the invention are much improved over the state of the art wherein excess hydrogen peroxide is used because of the greatly and surprisingly improved effectiveness of the biocide.

The following specific examples in which percentages are by weight and all reagents are good commercial grade, are presented to illustrate various aspects of the present invention but are not to be construed as limitations thereof.

EXAMPLE 1

Untreated clay (60% solids) samples were obtained from a bisulfite-bleached, commercial grade, kaolin clay process. The samples were divided into 50 g aliquots.

Bisulfite content in the samples was determined with Merck Quant Sulfite Test Strips. The clay solids were separated by centrifugation and the test strip was submerged into the aqueous portion. The test strip was then compared to a standard to quantify the bisulfite content. The bisulfite level was found to be 180 ppm.

Six clay samples were then treated with sodium nitrite in amounts ranging from 0 to 250 ppm and then incubated at 40° C. for 30 minutes. The bisulfite content in the samples was then redetermined using the test strips described above.

The clay samples were further treated with 15 ppm of a 3:1 mixture of CMI:MI and then stored overnight before being placed in a 40° C. oven.

The samples were analyzed for 3-isothiazolone biocide effectiveness after 2, 7, and 14 days by reverse phase HPLC, utilizing an ultraviolet detector. The samples were diluted 1:5 in deionized water prior to analysis.

The results are reported in Table 1.

TABLE 1

Analysis of 3-Isothiazolone Biocide
After Pretreatment with Sodium Nitrite

| Time (days) | NaNO$_2$ (ppm) | % Isothiazolone Remaining |
|---|---|---|
| 2 | 0 | 7 |
|  | 50 | 23 |
|  | 100 | 29 |
|  | 150 | 87 |
|  | 200 | 100 |
|  | 250 | 105 |
| 7 | 0 | <13 |
|  | 150 | 82 |
|  | 200 | 103 |
|  | 250 | 103 |
| 14 | 0 | <8 |
|  | 150 | 79 |
|  | 200 | 98 |
|  | 250 | 97 |

EXAMPLE 2

Untreated kaolin clay (60% solids) samples were collected, divided into 50 g aliquots, and treated for bisulfite levels as described in Example 1. These clay samples were found to contain 250 ppm bisulfite before pretreatment with nitrite.

Following bisulfite determination, the samples were treated as described in Example 1.

The samples were then analyzed for isothiazolone as described above after 2 and 7 days.

The results are reported in Table 2.

TABLE 2

Analysis of 3-Isothiazolone Biocide
After Pretreatment with Sodium Nitrite

| Time (days) | NaNO$_2$ (ppm) | % Isothiazolone Remaining |
|---|---|---|
| 2 | 0 | <5 |
|  | 50 | 41 |
|  | 100 | 68 |
|  | 150 | 93 |
|  | 200 | 97 |
|  | 250 | 108 |
| 7 | 0 | <5 |
|  | 50 | 25 |
|  | 100 | 55 |
|  | 150 | 86 |
|  | 200 | 92 |
|  | 250 | 106 |

EXAMPLE 3—COMPARATIVE

This example demonstrates the significant difference in the effect of nitrites versus nitrates with no pretreatment.

Samples containing sifulfite (100 ppm) in phosphate buffered water (pH 7, 40° C.) were prepared. To these samples was added 100 or 200 ppm of oxidant (either a nitrite or a nitrate). The samples were then incubated for 30 minutes at 40° C. After incubation, 15 ppm or 3-isothiazolone (a 3:1 mixture of CMI:MI) was added, the control contained 3-isothiazolone and bisulfite in buffered water.

The samples were analyzed for 3-isothiazolone after 1,7, and 14 days. The relative concentration of isothiazolone was determined by reverse phase HPLC, utilizing an ultraviolet detector.

The 3-isothiazolone was considered effective when >85% of the total remained. The results are reported in Table 3.

TABLE 3

Comparsion with Nitrates

| Oxidant | Oxidant (ppm) | 3-Isothiazolone Effectiveness (days) |
|---|---|---|
| None (control) | 0 | <1 |
| Sodium nitrite | 200 | 14 |
| Sodium nitrite | 100 | 14 |
| Sodium nitrate (comparative) | 200 | <1 |
| Sodium nitrate (comparative) | 100 | <1 |
| Calcium nitrite | 200 | 14 |
| Calcium nitrite | 100 | 14 |
| Calcium nitrate (comparative) | 200 | <1 |
| Calcium nitrate (comparative) | 100 | <1 |
| Magnesium nitrate (comparative) | 200 | <1 |
| Magnesium nitrate (comparative) | 100 | <1 |

EXAMPLE 4—Comparative

This example demonstrates the significant difference in the effect of hydrogen peroxide versus TBHP.

Samples containing bisulfite, oxidant, and 3-isothiazolone were prepared as described in Example 3. The oxidant used was either hydrogen peroxide or TBEP.

These samples were analyzed as described in Example 3. The results are reported in Table 4.

TABLE 4

Comparative Effect of Hydrogen Peroxide vs TBHP

| Oxidant | Oxidant (ppm) | 3-Isothiazolone Effectiveness (days) |
|---|---|---|
| None (control) | 0 | <1 |
| Hydrogen peroxide (comparative) | 200 | <1 |
| Hydrogen peroxide (comparative) | 100 | <1 |
| tert-Butyl hydroperoxide | 200 | 14 |
| tert-Butyl hydroperoxide | 100 | 14 |

While this invention has been described in sufficient detail for those skilled in the art to be able to make and use it, various modifications, and improvements should become apparent from the foregoing disclosure without departing from the spirit and scope of the invention.

What is claimed is:

1. A method of treating and preserving mineral slurries containing nucleophiles comprising introducing to a mineral slurry containing nucleophiles from 10 to 2000 ppm by weight, based on slurry, if nitride compound or tert-butyl hydroperoxide, maintaining the temperature of said slurry at least about 30° C., and at least 10 minutes thereafter introducing to said slurry a microbicially-effective amount of a 3-isothiazolone biocide.

2. Method according to claim 1 wherein said nitride compound is selected from the group consisting of sodium nitride, calcium nitride, and potassium nitrite.

3. Method according to claim 1 wherein said nitrite compound is introduced in an amount of about 100 to 200 ppm.

4. Method according to claim 1 wherein said tert-butyl hydroperoxide is introduced in an amount of about 25 to 750 ppm by weight based on slurry.

5. Method according to claim 4 wherein said tert-butyl hydroperoxide is introduced in an amount of about 25 to 750 ppm by weight based on slurry.

6. Method according to claim 1 wherein said biocide is introduced about 15 to 40 minutes after said nitrite ion is introduced.

7. Method according to claim 1 wherein said biocide is one or more 3-isothiazolone compounds selected from the group consisting of 5-chloro-2-methyl-3-isothiazolone; 2-methyl-3-isothiazolone; 2-n-octyl-3-isothiazolone; 4,5-dichloro-2-n-octyl -3-isothiazolone; benzisothiazolone; and 2-methyl-4,5-trimethylene-3-isothiazolone.

8. Method according to claim 1 wherein said biodde is introduced in an amount of about 1 to 150 ppm by weight based on slurry.

9. Method according to claim 8 wherein said biocide is introduced in an amount of about 5 to 25 ppm.

* * * * *